(12) United States Patent
Kobbe

(10) Patent No.: US 7,119,712 B2
(45) Date of Patent: Oct. 10, 2006

(54) DATA RECOVERY SCHEME IN THERMOMETER SYSTEM

(75) Inventor: Rick Allen Kobbe, Powell Butte, OR (US)

(73) Assignee: Mini-Mitter Company, Inc., Bend, OR (US)

( * ) Notice: Subject to any disclaimer, the term of this patent is extended or adjusted under 35 U.S.C. 154(b) by 394 days.

(21) Appl. No.: 10/666,475

(22) Filed: Sep. 19, 2003

(65) Prior Publication Data

US 2004/0076183 A1  Apr. 22, 2004

Related U.S. Application Data

(60) Provisional application No. 60/412,252, filed on Sep. 19, 2002.

(51) Int. Cl.
| | |
|---|---|
| *G08C 19/16* | (2006.01) |
| *G08C 19/12* | (2006.01) |
| *H04J 3/24* | (2006.01) |
| *G01K 7/00* | (2006.01) |
| *H03M 13/00* | (2006.01) |

(52) U.S. Cl. ........................ 340/870.01; 340/870.17; 370/474; 370/473; 374/170; 374/183; 714/758

(58) Field of Classification Search ............ 340/870.1, 340/870.01, 870.05, 870.17, 870.19; 370/474, 370/473; 374/170, 183; 600/300, 549; 714/758
See application file for complete search history.

(56) References Cited

U.S. PATENT DOCUMENTS

| | | | | |
|---|---|---|---|---|
| 5,381,136 A | * | 1/1995 | Powers et al. | 340/539.26 |
| 6,020,830 A | * | 2/2000 | Gannon et al. | 340/870.13 |
| 6,181,258 B1 | * | 1/2001 | Summers et al. | 340/870.28 |
| 6,300,871 B1 | * | 10/2001 | Irwin et al. | 340/539.28 |
| 2005/0010850 A1 | * | 1/2005 | Driessen et al. | 714/758 |

* cited by examiner

*Primary Examiner*—Jeffery Hofsass
*Assistant Examiner*—Sisay Yacob
(74) *Attorney, Agent, or Firm*—Richard J. Coldren; Timothy A. Nathan; Michael W. Haas

(57) ABSTRACT

A telemetry system includes a transmitter unit that measures a first value of a parameter, incorporates the first value in a first data packet and transmits the first data packet, and measures a second value of the parameter, incorporates the second value and the first value in a second data packet and transmits the second data packet. A receiver unit periodically receives a signal and generates a sequence of bits therefrom, determines whether the sequence of bits includes a payload that meets a predetermined standard and, if so, recovers a more recent datum from the payload else enters a data recovery mode. In the data recovery mode, the receiver unit receives a transmission signal and generates a second sequence of bits and determines whether the second sequence of bits contains a payload that meets the predetermined standard and, if so, recovers both a more recent datum and a less recent datum from the payload.

14 Claims, 2 Drawing Sheets

| TIME | 12:34:09 | 12:35:01 | 12:36:24 |
|---|---|---|---|
| TEMPERATURE | 37.89 | 37.90 | 37.92 |
| PACKET VALUES CURRENT DATUM | 37.89 | ERROR | 37.92 |
| PRIOR DATUM | UNKNOWN | ERROR | 37.90 |
| DATA SEQUENCE | X<br>37.89 | X<br>37.89<br>ERR | X<br>37.89<br>37.90<br>37.92 |

FIG. 2

DATA RECOVERY SCHEME IN THERMOMETER SYSTEM

CROSS-REFERENCE TO RELATED APPLICATION

This application claims benefit of the date of filing of U.S. Provisional Application No. 60/412,252 filed Sep. 19, 2002.

STATEMENT REGARDING FEDERALLY SPONSORED RESEARCH OR DEVELOPMENT

This invention was made with United States government support under Contract No. DAMD 17-01-C-0022 awarded by the Department of the Army. The United States government has certain rights in the invention.

BACKGROUND OF THE INVENTION

This invention relates to a data recovery scheme for use in a telemetric measurement system, and particularly for use in a telemetric thermometer system.

U.S. patent application Ser. No. 10/017,098 filed Dec. 12, 2001 (now U.S. Pat. No. 6,629,776), the entire disclosure of which is hereby incorporated by reference herein for all purposes, discloses a telemetric thermometer system that comprises a transmitter unit and a receiver unit. The transmitter unit includes a sensor device for sensing temperature and a radio transmitter that creates and transmits packets having temperature values encoded therein. The receiver unit includes a radio receiver for receiving packets transmitted by the transmitter unit and recovering the temperature values that are encoded in the packets. The transmitter unit and the receiver unit include respective clock oscillators and internal dividers for generating a common clock frequency that is the same for both units, so that time measured by clock cycles of the receiver unit passes at the same rate as time measured by clock cycles of the transmitter unit.

The transmitter unit and the receiver unit each divide future time into operating intervals of fifteen seconds and divide each operating interval into an active interval and guard interval. Each active interval is further divided into 256 transmission slots of about 47 milliseconds.

The transmitter unit and receiver unit include respective functionally-identical pseudo-random number generators (PNGs). When the transmitter unit is first manufactured, it is placed in a "sleep" mode in which its PNG is inactive. When the transmitter unit is brought into service, it is activated by the receiver unit. Both PNGs commence operation at the same time and are seeded with the same value. Accordingly, the two PNGs operate in synchronism even though they are not connected together. For each operating interval, the PNG of the transmitter unit calculates a number in the range 1–256 and the PNG of the receiver unit calculates the same number. The number calculated by the two PNGs is used to select one of the 256 transmission slots in the operating interval. The transmitter unit transmits a packet during the transmission slot and does not otherwise transmit packets. The receiver unit is in an active state for the duration of the transmission slot, and in the active state the radio receiver is on. If the radio receiver receives a valid transmission packet, it provides an output signal from which the temperature value encoded in the transmission packet can be recovered. Otherwise, the receiver unit is in an idle state, in which the radio receiver is off.

In a proposed implementation of the thermometer described in U.S. patent application Ser. No. 10/017,098, it is possible that the receiver unit will be unable to recover a temperature value for every transmission by the transmitter unit, for example due to failure of a cyclic redundancy check or noise. The receiver unit of the telemetry system may serve several transmitter units. It is possible that two transmitter units will select the same transmission slot, in which case collision of the transmissions by the respective radio transmitters may prevent the receiver from receiving a valid packet. It is desirable that loss of data should be avoided or minimized.

SUMMARY OF THE INVENTION

In accordance with a first aspect of the invention there is provided a transmitter unit comprising a sensor for generating a sensor signal having a characteristic that is representative of a variable, a measurement device for receiving the sensor signal, repeatedly measuring said characteristic, and generating an output signal representing a succession of measured values of the characteristic, a packetizer for receiving the measured values from the measurement device and generating a succession of transmission packets each including a more recently measured value and a less recently measured value, wherein the more recently measured value that is included in an earlier packet is included in a later packet as the less recently measured value, and a transmitter for receiving the succession of transmission packets from the packetizer and transmitting the succession of transmission packets.

In accordance with a second aspect of the invention there is provided a receiver unit comprising a receiver for receiving a signal and recovering a sequence of bits from the received signal, a packet check means for determining whether the sequence of bits meets a predetermined standard and, if so, recovering a more recent datum from the sequence of bits else entering a data recovery mode and determining whether a sequence of bits subsequently recovered from the transmission signal meets said predetermined standard and, if so, recovering both a more recent datum and a less recent datum from the subsequent sequence of bits.

In accordance with a third aspect of the invention there is provided a telemetry system comprising a transmitter unit and a receiver unit wherein the transmitter unit comprises a sensor for generating a sensor signal having a characteristic that is representative of a variable, a measurement device for receiving the sensor signal, repeatedly measuring said characteristic, and generating an output signal representing a succession of measured values of the characteristic, a packetizer for receiving the measured values from the measurement device and generating a succession of transmission packets each including a more recently measured value and a less recently measured value, wherein the more recently measured value that is included in an earlier packet is included in a later packet as the less recently measured value, and a transmitter for receiving the succession of transmission packets from the packetizer and transmitting the succession of transmission packets; and the receiver unit comprises a receiver for receiving a signal and recovering a sequence of bits from the received signal, a packet check means for determining whether the sequence of bits meets a predetermined standard and, if so, recovering a more recent datum from the sequence of bits else entering a data recovery mode and determining whether a sequence of bits subsequently recovered from the transmission signal meets said predetermined standard and, if so, recovering both a more recent datum and a less recent datum from the subsequent sequence of bits.

In accordance with a fourth aspect of the invention there is provided a method of operating a telemetric transmitter unit that periodically measures the value of a parameter and periodically and sequentially transmits the measured values, the method comprising measuring a first value of the parameter, incorporating the first value in a first data packet, and transmitting the first data packet, and measuring a second value of the parameter, incorporating the second value and the first value in a second data packet, and transmitting the second data packet.

In accordance with a fifth aspect of the invention there is provided a method of operating a telemetric receiver unit, the method comprising periodically receiving a signal and generating a sequence of bits therefrom, determining whether the sequence of bits includes a payload that meets a predetermined standard and, if so, recovering a more recent datum from the payload else entering a data recovery mode, and in the data recovery mode receiving a signal and generating a second sequence of bits and determining whether the second sequence of bits contains a payload that meets said predetermined standard and, if so, recovering both a more recent datum and a less recent datum from the payload.

In accordance with a sixth aspect of the invention there is provided a method of operating a telemetry system that comprises a transmitter unit and a receiver unit, wherein the transmitter unit operates in accordance with a method that comprises measuring a first value of a parameter, incorporating the first value in a first data packet and transmitting the first data packet, and measuring a second value of the parameter, incorporating the second value and the first value in a second data packet and transmitting the second data packet; and the receiver unit operates in accordance with a method that comprises periodically receiving a signal and generating a sequence of bits therefrom, determining whether the sequence of bits includes a payload that meets a predetermined standard and, if so, recovering a more recent datum from the payload else entering a data recovery mode, and in the data recovery mode receiving a transmission signal and generating a second sequence of bits and determining whether the second sequence of bits contains a payload that meets said predetermined standard and, if so, recovering both a more recent datum and a less recent datum from the payload.

BRIEF DESCRIPTION OF THE DRAWINGS

For a better understanding of the invention, and to show how the same may be carried into effect, reference will now be made, by way of example, to the accompanying drawings, in which FIG. 2 is a timing diagram illustrating operation of the system shown in FIG. 1.

DETAILED DESCRIPTION

Figure 1:
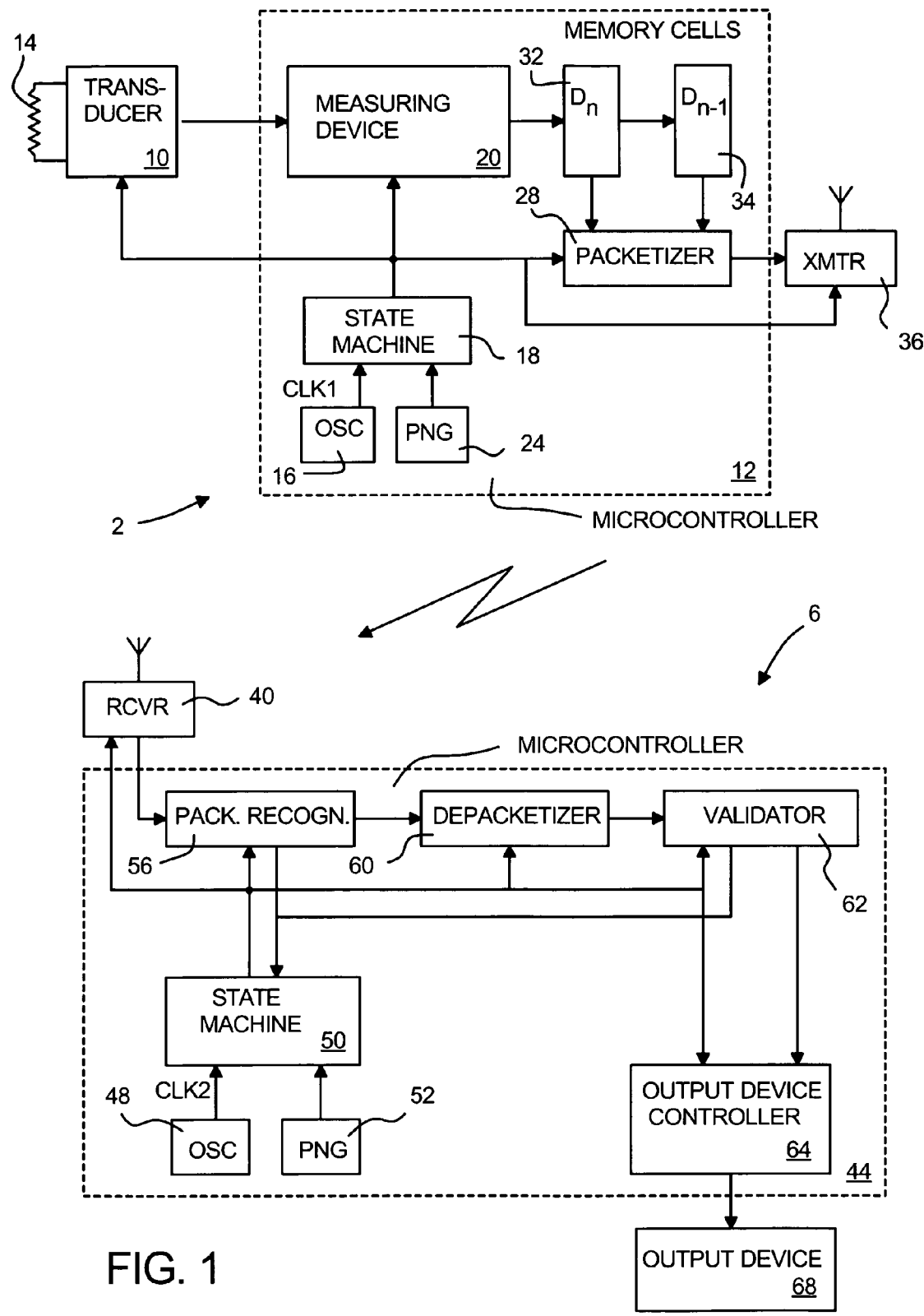
FIG. 1 is a schematic block diagram illustrating a telemetric thermometer system embodying the present invention.

Referring to FIG. 1, the thermometer system comprises a transmitter unit 2 and a receiver unit 6. The transmitter unit 2 includes a transducer 10 having a sensor element 14 (illustrated by way of example as a thermistor) that is in thermal equilibrium with an object (not shown) whose temperature is to be measured. The transducer 10 develops a binary electrical signal having a characteristic, such as pulse frequency, that varies as a function of the temperature of the sensor element.

The transmitter unit also comprises a microcontroller 12. The microcontroller includes a clock oscillator 16 that generates a clock signal CLK. The microcontroller 12 implements a finite state machine 18, a measuring device 20 (for example, a frequency measuring device in the event that the characteristic that varies as a function of temperature is signal frequency), a pseudo-random number generator (PNG) 24, and a packetizer 28.

The state machine 18 is responsive to the clock oscillator 16 for controlling operation of the transducer, the measuring device, the PNG and the packetizer.

The state machine 18 divides time, as measured by the clock signal CLK1, into fifteen second operating intervals and divides each operating interval into an active interval and a guard interval. The state machine 18 further divides each active interval into 256 telemetry slots, with each telemetry slot being defined by a time point.

For each operating interval, the PNG 24 calculates a number in the range 1–256 using a pseudo-random number generation algorithm. The state machine 18 uses the calculated number to specify the telemetry slot that will be used in the next active interval. During each guard interval the state machine initiates a measurement sequence. Just prior to the specified telemetry slot, the state machine initiates the transmission sequence.

In the measurement and transmission sequence, the measuring device 20 measures the value of the characteristic of the electrical signal developed by the transducer, calculates a temperature datum based on the measured value of the characteristic, and generates a digital word representing the temperature value. The measuring device supplies this digital word to a memory cell 32 and the state machine 18 deactivates the measuring device. Prior to loading the digital word for the next operating interval into the memory cell 32, the state machine shifts the digital word currently stored in the memory cell 32 to a second memory cell 34, overwriting the digital word that was previously stored in that memory cell. Thus, the two memory cells 32 and 34 contain, respectively, the digital word $D_n$ representing the value returned by the most recent measurement and the digital word $D_{(n-1)}$ representing the value returned by the immediately preceding measurement. The packetizer reads the two digital words stored in the memory cells 32 and 34 respectively and constructs a transmission packet.

The packet that is constructed by the packetizer 28 is composed of a preamble, a sync word, payload bits (the digital words read from the memory cells 32 and 34 and possibly other data, such as a transmitter ID and a time value), and an error detection byte for protecting against loss of data or decoding errors. Let us assume for the purpose of discussion that the total number of bits in the packet is N1+N2 and that the preamble is composed of N1 bits.

Once the packet has been constructed, the state machine 18 activates a radio transmitter 36. The packetizer 28 generates a packet signal that represents the bit sequence of the packet and supplies the packet signal to the radio transmitter 36, which modulates an RF carrier in accordance with the packet signal for wireless transmission of the packet signal during the telemetry slot specified by the state machine 18.

The receiver unit 6 includes a radio receiver 40 and a microcontroller 44. The microcontroller 44 includes a clock oscillator 48 that is divided to run at the same frequency as the clock oscillator 16. The microcontroller implements a finite state machine 50, a PNG 52, a packet recognizer 56, a depacketizer 60, a packet validator 62 and an output device controller 64.

The state machine 50 is responsive to the clock oscillator 48 for controlling operation of the receiver 40, the packet recognizer 56, the PNG 52, the packetizer 60 and the output device controller 64. The state machine 50 divides time measured by the clock signal CLK2 generated by the oscillator 48 in similar fashion to that in which the state machine 18 divides time measured by the clock signal CLK1. The two state machines 18 and 50 are synchronized so that the telemetry slots defined by the state machine 18 coincide in time with the telemetry slots defined by the state machine 50.

The receiver PNG 52 operates in the same manner as the transmitter PNG 24. For each operating interval of the system, the receiver PNG 52 calculates a number in the range 1–256. This number, which is the same as the number calculated by the transmitter PNG 24, is used to specify a telemetry slot in which the microcontroller 44 initiates a reception and interpretation sequence.

In the reception and interpretation sequence, the state machine 50 activates the radio receiver 40 and the packet recognizer 56. The radio receiver is tuned to the carrier frequency of the transmitter 36 and outputs a digital reception signal to the packet recognizer 56.

The packet recognizer examines each set of N1 successive bits received from the radio receiver during the telemetry slot and determines whether the sequence of bits matches the sequence in the packet preamble. If the packet recognizer 56 identifies the bit sequence of the preamble within a predetermined interval after initiation of the reception and interpretation sequence, it passes the succeeding N2 bits to the depacketizer 60 and the state machine 50 immediately deactivates the receiver 40 and the packet recognizer 56. If the packet recognizer does not identify the bit sequence of the preamble within the predetermined interval, the packet recognizer sets a flag and, in response, the state machine 50 deactivates the receiver and the packet recognizer and enters a data recovery state.

If the packet recognizer identifies the preamble sequence and passes the succeeding N2 bits to the depacketizer 60, the depacketizer separates the remaining components of the packet (sync word, payload bits and error detection byte) and provides these components to the packet validator 62. The packet validator determines whether these components are syntactically valid, e.g. whether the error detection byte has the correct value and whether the payload bits represent values that are within the expected ranges. If the remaining packet components pass the packet validator tests, the packet validator makes the two temperature data available to the output device controller 64; otherwise, the packet validator sets a flag and the state machine 50 enters the data recovery state.

Assuming that the remaining packet components passed the packet validator tests in the current operating interval, the subsequent behavior of the output device controller depends on whether the state machine 50 is currently in the data recovery state, i.e. whether the receiver unit received a syntactically valid packet in the preceding operating interval. If the state machine 50 is not in the data recovery state, the output device controller 64 reads only the more recent temperature datum from the packet validator. The less recent datum is redundant and is discarded, because the same datum was extracted from the previous packet. The output device controller 64 calculates a temperature value based on a desired scale, e.g. the Celsius scale, and outputs the temperature value to an output device 68, such as a display or recording device. The display or recording device thus provides a sequence of temperature values.

Conversely, if the state machine 50 is in the data recovery state, which implies that there is a missing entry in the sequence of temperature values received by the output device, the output device controller reads both the temperature data from the packet validator, calculates the two corresponding temperature values based on the desired scale and supplies the two temperature values to the output device, which uses the less recent temperature value to fill the blank in the sequence of temperature values.

FIG. 2 illustrates by way of example the time points for three successive operating intervals and the temperature data associated with the time points respectively (expressed as temperature values in degrees Celsius). FIG. 2 illustrates the temperature values corresponding to the temperature data that are recovered at the receiver unit and the sequence of temperature values provided by the output device, when viewed at the end of the three consecutive operating intervals.

The foregoing description of the operation of the receiver unit is based on the microcontroller 44 implementing only one PNG 52. Since the PNG generates only one number for each operating interval, this implies that the illustrated receiver unit serves only a single transmitter unit. It is desirable that the receiver unit should be able to serve multiple transmitter units, and this may be accomplished by use of a more complex PNG sequencer, which employs multiple seed values, transferred from the transmitter units respectively, to execute an algorithm that returns the numbers that are generated by the individual transmitter unit PNGs.

It will be seen that in the illustrated system the transmitter unit transmits each temperature datum to the receiver unit twice. Due to the low probability that two consecutive transmissions by the transmitter unit will not be correctly received by the receiver unit, this method enables the recovery of approximately 95% of the data that would otherwise be lost due to missed packets, collisions and CRC errors.

It would be possible to transmit two previous temperature data along with the current datum and this would allow the system to provide a complete record even if two consecutive transmissions were lost. In this case, three memory cells would be required in the transmitter microcontroller. The invention is not restricted to transmitting just one or two previous temperature data along with the current datum, but it will be appreciated that each increase in the number of temperature data increases the length of the data packet and leads to a higher probability of overlap among transmissions from other sensors and a higher probability of collisions.

Although the transmitter unit described with reference to FIG. 1 transmits the most recent temperature datum and the immediately preceding temperature datum, it would be possible, particularly if the output device 68 provides a record for subsequent viewing and immediate warning of a temperature value passing out of range is not critical, to transmit, for example, the previous datum and the datum that immediately precedes the previous datum. Further, it is not essential that the data that are transmitted in a given telemetry slot be consecutive data. It is necessary only that each datum be transmitted at least twice and that the receiver unit and transmitter unit operate in accordance with corresponding rules so that if the receiver unit does not receive a valid packet it is able to predict when a more recent datum of the packet that was not validly received will be transmitted for the second time.

Although the invention has been described with reference to a thermometer, the principles underlying the invention are applicable to other sensor types. For example, a physiological sensor might report heart rate at 15 second intervals. If, in each transmission, the sensor reports not only the current heart rate but also the heart rate measured fifteen seconds previously, the system is substantially immune to loss of a single transmission. Likewise, the principles could applied to gross motor activity measurements, movements associated with normal sleep and disrupted sleep, blood oxygen saturation levels, ECG signals, ventilation values, and other parameter values for which the system has a remote, telemetric sensor. Further, the invention is not limited to measurement of physiological variables and may be applied, for example, to measurement of variables in industrial processes.

The microcontroller that is included in the transmitter unit is illustrated as being composed of several discrete functional blocks, but it will be appreciated by those skilled in the art that this manner of illustration has been selected for convenience in discussing signal flow. Further, it will be appreciated that the allocation of functions among the blocks is at least somewhat arbitrary and that a different allocation could be chosen if desired. Of course, similar observations apply to the microcontroller that is included in the receiver unit.

It will be appreciated that the invention is not restricted to the particular embodiment that has been described, and that variations may be made therein without departing from the scope of the invention as defined in the appended claims and equivalents thereof. For example, although the foregoing description refers to the temperature values being calculated by the output device controller, the temperature values might be calculated by the measuring device 20, such that the temperature data correspond directly to the temperature values on the desired scale. Unless the context indicates otherwise, a reference in a claim to the number of instances of an element, be it a reference to one instance or more than one instance, requires at least the stated number of instances of the element but is not intended to exclude from the scope of the claim a structure or method having more instances of that element than stated.

The invention claimed is:

1. A transmitter unit comprising:
a sensor for generating a sensor signal having a characteristic that is representative of a variable,
a measurement device for receiving the sensor signal, repeatedly measuring said characteristic, and generating an output signal representing a succession of measured values of the characteristic,
a packetizer for receiving the measured values from the measurement device and generating a succession of transmission packets each including a more recently measured value and a less recently measured value, wherein the more recently measured value that is included in an earlier packet is included in a later packet as the less recently measured value, and
a transmitter for receiving the succession of transmission packets from the packetizer and transmitting the succession of transmission packets.

2. A transmitter unit according to claim 1, wherein the packetizer repeatedly receives the most recently measured value from the measurement device and the immediately preceding measured value from the measurement device.

3. A transmitter unit according to claim 1, comprising a control means for defining a succession of active intervals, and wherein the transmitter transmits the transmission packets during respective active intervals.

4. A transmitter unit according to claim 3, wherein the control means divides each active interval into multiple telemetry slots and selects a telemetry slot for each active interval, and the transmitter device transmits the transmission packet during the selected telemetry slot.

5. A transmitter unit according to claim 3, wherein the measurement device measures the characteristic once per active interval and the packetizer received a more recently measured value and a less recently measured value from the measurement device for each active interval.

6. A receiver unit comprising:
a receiver for receiving a signal and recovering a sequence of bits from the received signal,
a packet check means for determining whether the sequence of bits meets a predetermined standard and, if so, recovering a more recent datum from the sequence of bits else entering a data recovery mode and determining whether a sequence of bits subsequently recovered from the transmission signal meets said predetermined standard and, if so, recovering both a more recent datum and a less recent datum from the subsequent sequence of bits.

7. A receiver unit according to claim 6, wherein the packet check means comprises a packet recognizer and a packet validator, wherein the packet recognizer determines whether the sequence of bits includes a preamble sequence and, if so, passes a predetermined number of subsequent bits to the packet validator, and wherein the packet validator determines whether said predetermined number of subsequent bits includes an error-free payload.

8. A receiver unit according to claim 6, wherein the packet check means determines whether the sequence of bits recovered from the received signal contains a payload that meets a predetermined standard by determining whether the sequence of bits includes a predetermined preamble sequence.

9. A receiver unit according to claim 6, wherein the packet check means determines whether the sequence of bits recovered from the received signal includes an error-free payload.

10. A telemetry system comprising a transmitter unit and a receiver unit wherein:
the transmitter unit comprises:
a sensor for generating a sensor signal having a characteristic that is representative of a variable,
a measurement device for receiving the sensor signal, repeatedly measuring said characteristic, and generating an output signal representing a succession of measured values of the characteristic,
a packetizer for receiving the measured values from the measurement device and generating a succession of transmission packets each including a more recently measured value and a less recently measured value, wherein the more recently measured value that is included in an earlier packet is included in a later packet as the less recently measured value, and
a transmitter for receiving the succession of transmission packets from the packetizer and transmitting the succession of transmission packets; and
the receiver unit comprises:
a receiver for receiving a signal and recovering a sequence of bits from the received signal,
a packet check means for determining whether the sequence of bits meets a predetermined standard and, if so, recovering a more recent datum from the sequence of bits else entering a data recovery mode and determining whether a sequence of bits subsequently recovered from the transmission signal meets said predetermined standard and, if so, recovering both a more recent datum and a less recent datum from the subsequent sequence of bits.

11. A telemetry system according to claim 10, wherein the transmitter is a wireless transmitter and the receiver is a radio receiver.

12. A method of operating a telemetric transmitter unit that periodically measures the value of a parameter and periodically and sequentially transmits the measured values, the method comprising:

measuring a first value of the parameter, incorporating the first value in a first data packet, and transmitting the first data packet, and measuring a second value of the parameter, incorporating the second value and the first value in a second data packet, and transmitting the second data packet.

13. A method of operating a telemetric receiver unit, the method comprising:

periodically receiving a signal and generating a sequence of bits therefrom, determining whether the sequence of bits includes a payload that meets a predetermined standard and, if so, recovering a more recent datum from the payload else entering a data recovery mode, and in the data recovery mode receiving a signal and generating a second sequence of bits and determining whether the second sequence of bits contains a payload that meets said predetermined standard and, if so, recovering both a more recent datum and a less recent datum from the payload.

14. A method of operating a telemetry system that comprises a transmitter unit and a receiver unit, wherein the transmitter unit operates in accordance with a method that comprises:

measuring a first value of a parameter, incorporating the first value in a first data packet and transmitting the first data packet, and measuring a second value of the parameter, incorporating the second value and the first value in a second data packet and transmitting the second data packet;

and the receiver unit operates in accordance with a method that comprises:

periodically receiving a signal and generating a sequence of bits therefrom, determining whether the sequence of bits includes a payload that meets a predetermined standard and, if so, recovering a more recent datum from the payload else entering a data recovery mode, and in the data recovery mode receiving a transmission signal and generating a second sequence of bits and determining whether the second sequence of bits contains a payload that meets said predetermined standard and, if so, recovering both a more recent datum and a less recent datum from the payload.

* * * * *